United States Patent [19]
Kilbourn et al.

[11] Patent Number: 5,296,466
[45] Date of Patent: Mar. 22, 1994

[54] INHIBITION OF NITRIC OXIDE-MEDIATED HYPOTENSION AND SEPTIC SHOCK WITH IRON-CONTAINING HEMOPROTEIN

[75] Inventors: Robert G. Kilbourn, Houston, Tex.; Joseph De Angelo, Hamtramck, Mich.; Joseph Bonaventura, Beaufort, N.C.

[73] Assignees: Board of Regents, The University of Texas System, Austin, Tex.; Strohtech, Inc., Detroit, Mich.; Duke University, Durham, N.C.

[21] Appl. No.: 838,603

[22] Filed: Feb. 19, 1992

[51] Int. Cl.$^5$ .......................... A61K 37/02
[52] U.S. Cl. .................................. 514/6
[58] Field of Search ........................... 514/6

[56] References Cited

U.S. PATENT DOCUMENTS

| | | | |
|---|---|---|---|
| 4,061,736 | 12/1977 | Morris et al. | 424/177 |
| 4,584,130 | 4/1986 | Bucci et al. | 260/112 |
| 4,598,064 | 7/1986 | Walder | 514/6 |
| 4,751,068 | 6/1988 | Bickar et al. | 423/437 |
| 5,028,627 | 7/1991 | Kilbourn et al. | 514/12 |
| 5,082,642 | 1/1992 | Bickar et al. | 423/402 |

FOREIGN PATENT DOCUMENTS

| | | |
|---|---|---|
| US90/02654 | 7/1990 | PCT Int'l Appl. |
| US90/05199 | 9/1990 | PCT Int'l Appl. |
| WO91/04023 | 4/1991 | PCT Int'l Appl. |
| WO91/04024 | 4/1991 | PCT Int'l Appl. |
| WO91/84023 | 4/1991 | PCT Int'l Appl. |
| WO93/00893 | 1/1993 | PCT Int'l Appl. |

OTHER PUBLICATIONS

Wang et al., Nitric oxide hemoglobin in mice and rats in endotoxic shock, *Chemical Abstracts*, vol. 115, No. 15, issued 1991, Oct. 14, p. 659m, col. 1, the abstract-No. 156 199a, Life Sci. 1991, 49(11), PL55-PL60.

Westenberger et al., Formation of free radicals and nitric oxide derivative of hemoglobin in rats during shock syndrome, *Chemical Abstracts*, vol. 114, No. 21, issued 1991, May 27, p. 597, col. 2-p. 598, col. 1, the abstract-No. 204 845m, Free Radical Res. Commun. 1990, 11(1-3), 167-178.

Wang et al., "Nitric Oxide Hemoglobin in Mice and Rats in Endotoxic Shock", *Lifesciences*, 49, p155-p160, 1991.

Westenberger et al., "Formation of Free Radicals and Nitric Oxide Derivative of Hemoglobin in Rats During Shock Syndrome", *Free Radical Res. Commun.*, 11, 167-178, 1990.

Kosaka et al., "Detection of Nitric Oxide Production in Lipopoysaccharide-Treated Rats by ESR Using Carbon Monoxide Hemoglobin", *Biochem. and Biophys. Res. Commun.*, 1119-1124, Apr. 30. 1992.

Stamler et al., "Biochemistry of Nitric Oxide and Its Redox-Activated Forms", *Science*, 258, 1898-1902, 1992.

Koshland, Jr., "Editorial-The Molecule of the Year", (*Science*, 258, 1861) 1992.

Culotta et al., "No News Is Good News", *Science*, 258, 1862-1865, 1992.

Bickar et al., "Carbon Monoxide-Driven Reduction of Ferric Heme and Heme Proteins," *Journal of Biological Chemistry*, 259(17): 10777-10783, 1984, published in USA.

Martin et al., "Selective Blockade of Endothelium-Dependent and Glyceryl Trinitrate-Induced Relaxation by Hemoglobin and by Methylene Blue in the Rabbit Aorta," *The Journal of Pharmacology and Experimental Therapeutics*, 232(3):708-716, 1985, published in USA.

(List continued on next page.)

Primary Examiner—Michael G. Wityshyn
Assistant Examiner—Choon Koh
Attorney, Agent, or Firm—Arnold, White & Durkee

[57] ABSTRACT

The invention is directed to a method for the prophylaxis or treatment of an animal for deleterious physiological effects such as systemic hypotension caused by nitric oxide production induced by a biological response modifier. Examples of such biological response modifiers include but are not limited to a cytokine and an endotoxin. The invention is also directed to a method for the treatment of septic shock.

15 Claims, 1 Drawing Sheet

OTHER PUBLICATIONS

Buga et al., "Endothelium-Derived Nitric Oxide Relaxes Nonvascular Smooth Muscle," *European Journal of Pharmacology*, 161:61-72, 1989, published in Europe.

Stuehr et al., "Activated Murine Macrophages Secrete a Metabolite of Arginine with the Bioactivity of Endothelium-Derived Relaxing Factor and the Chemical Reactivity of Nitric Oxide," *J. Exp. Med.*, 169:1011-1020, 1989, published in USA.

Stuehr et al., "Synthesis of Nitrogen Oxides from L-Arginine by Macrophage Cytosol: Requirement for Inducible and Constitutive Components," *Biochemical and Biophysical Research Communications*, 161(2):420-426, 1989, published in USA.

Torti et al., "A Macrophage Factor Inhibits Adipocyte Gene Expression: An in Vitro Model of Cachexia," *Science*, 229:867-871, 1985, published in USA.

Palmer et al., "Vascular Endothelial Cells Synthesize Nitric Oxide from L-Arginine," *Nature*, 333:664-666, 1988, published in Europe.

Old, Lloyd J., "Tumor Necrosis Factor (TNF)," 230:630-632, 1985, published in USA.

Yoshida and Kasama, "Biotransformation of Nitric Oxide," *Environmental Health Perspectives*, 73:201-206, 1987, published in USA.

Schmidt et al., "Arginine is a Physiological Precursor of Endothelium-Derived Nitric Oxide," *European Journal of Pharmacology*, 154:213-216, 1988, published in Europe.

Reif and Simmons, "Nitric Oxide Mediates Iron Release from Ferritin," *Archives of Biochemistry and Biophysics*, 283(2):537-541, 1990, published in USA.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics*, 241(1):307-313, 1987, published in USA.

Kosaka et al., "The Interaction Between Nitrogen Oxides and Hemoglobin and Endothelium-Derived Relaxing Factor," *Free Radical Biology and Medicine*, 7:653-658, 1989, published in USA.

Chevion et al., "Iron-Nitrosyl Bond Configuration in Nitrosyl-Hemoproteins: A Comparative EPR Study of Hemoglobin A and Hemoglobin Kansas," *Israel Journal of Chemistry*, 15:311-317, 1976, published in Israel.

Collier and Vallance, "Second Messenger Role for NO Widens to Nervous and Immune Systems," *Trends in Pharmacological Sciences Including Toxicological Sciences*, Elseview Science Publishers, Ltd., front page and pp. 428-431, 1989, published in United Kingdom.

Ignarro et al., "Endothelium-Derived Relaxing Factor Produced and Released from Artery and Vein is Nitric Oxide," *Proc. Natl. Acad. Sci. USA*, 84:9265-9269, 1987, published in USA.

Murray et al., "Stabilization and Partial Characterization of Endothelium-Derived Relaxing Factor from Cultured Bovine Aortic Endothelial Cells," *Biochemical and Biophysical Research Communications*, 141(2):689-696, 1986, published in USA.

Marletta, Michael A., "Nitric Oxide: Biosynthesis and Biological Significance," name of publication unknown, Elseview Science Publishers, Ltd., pp. 448-493, 1989, published in United Kingdom.

Geokas et al., "Methemalbumin in the Diagnosis of Acute Hemorrhagic Pancreatitis," *Annals of Internal Medicine*, 81:483-486, 1974, published in USA.

Murray et al., "Measurement of Methaemalbumin in Plasma," *J. Clin. Path.*, 26:446-447, 1973, published in Europe.

Muller-Eberhard and Morgan, "Porphyrin-Binding Proteins in Serum," *Annals New York Academy of Sciences*, 224:624-649, 1975, published in USA.

Baur, Ernst W., "The Evolution of Methaemalbumin," *Comp. Biochem. Physiol.*, 30:657-664, 1969, published in Europe.

Chong et al., "Determination of Methaemalbumin in Plasma," *J. Clinical Pathology*, 20:211-212, 1967, published in Europe.

Marden et al., "Flash Photolysis of the Serum Albumin-Heme-CO Complex," *Biochemistry*, 28(10):4422-4426, 1989, published in USA.

Bonkovsky et al., "Intravenous Heme-Albumin in Acute Intermittent Prophyria: Evidence for Repletion of Depatic Hemoproteins and Regulatory Heme Pools," *The American Journal of Gastroenterology*, 86(8):1050-1056, 1991, published in USA.

Bone, Roger C., "The Pathogenesis of Sepsis," *Ann. Int. Med.* 115:457-469, 1991, published in USA.

Bone, Roger C., "A Critical Evaluation of New Agents for the Treatment of Sepsis," *JAMA* 266(12):1686-1691, 1991, published in USA.

(List continued on next page.)

OTHER PUBLICATIONS

Glauser, M. P., et al., "Septic Shock: Pathogenesis," *The Lancet*, 338:732-736, 1991, published in UK.

Johnston, J., "Molecular Science Sets Its Sights on Septic Shock," *J. NIH Res.* 3:61-65, 1991, Published in USA.

Moncada, S. and E. A. Higgs, "Endogenous Nitric Oxide: Physiology, Pathology, and Clinical Relevance," *Eur. J. Clin. Invest.* 21:361-374, 1991, published in Europe.

Moncada, S., et al., "The L-Arginine: Nitric Oxide Pathway," *J. Cardiovascular Pharm.* 7(Suppl. 3):S1-S9, 1991. Published in USA.

Moncada, S., et al., "Nitric Oxide: Physiology, Pathopysiology, and Pharmacology," *Pharmacological Reviews* 43(2):109-142. Published in USA. (1991).

Parratt, J. R., and J. C. Stoclet, "Possible Role of Nitric Oxide in Refractory Hypotension Associated with Sepsis and Endotoxaemia and with Multiple Organ Failure," *Applied Cardiopulmonary Pathophysiology* 4:143-149, 1991. Published in the Netherlands.

Snell, R. J., and J. E. Parrillo, "Cardiovascular Dysfunction in Septic Shock," *Chest* 99(4):1000-1009, 1991. Published in USA.

Wang, Q., et al., "Nitric Oxide Hemoglobin in Mice and Rats in Endotoxic Shock," *Life Sciences* 49:PL-55-60, 1991. Published in USA.

Kilbourn et al., "$N^G$-Methyl-L-arginine Inhibits Tumor Necrosis Factor-Induced Hypotension: Implications for the Involvement of Nitric Oxide," *Proc. Natl. Acad. Sci. USA*, 87:3629-3632, 1990, published in U.S.A.

Palmer et al., "Nitric Oxide Release Accounts for the Biological Activity of Endothelium-Derived Relaxing Factor," *Nature*, 327:524-526, 1987, published in England.

Moncada et al., "Generation of Prostacycline and Endothelium-Derived Relaxing Factor from Entothelial Cells," IN: Golles, G., Legran, J. Y., and Nurden, A., eds., *Biology and Pathology of Platelets-Vessel Wall Interactions*, pp. 289-304, 1986, published in London.

Kilbourn et al., "Activated Macrophages Secrete a Soluble Factor that Inhibits Mitochondrial Respiration of Tumor Cells," *The Journal of Immunology*, 133(5):2577-2581, 1984, published in Baltimore, MD.

Kilbourn & Belloni, "Endothelial Cell Production of Nitrogen Oxides in Response to Interferon $\gamma$ in Combination with Tumor Necrosis Factor, Interleukin-1, or Endotoxin," *Journal of the National Cancer Institute*, 82:772-776, 1990, published in U.S.A.

Aisaka et al., "$N^G$-Methylarginine, an Inhibitor of Endothelium-Derived Nitric Oxide Synthesis, is a Potent Pressor Agent in the Guinea Pig: Does Nitric Oxide Regulate Blood Pressure in Vivo?" *Biochemical and Biophysical Research Communications*, 160(2):881-886, 1989, published in San Diego, CA.

Vallance et al., "Effects of Endothelium-Derived Nitric Oxide on Peripheral Arteriolar Tone in Man," *Lancet*, 28:997-999, 1989, published in Great Britain.

Kilbourn et al., "Reversal of Endotoxin-Mediated Shock by $N^G$-Methyl-L-Arginine, an Inhibitor of Nitric Oxide Synthesis," *Biochemical and Biophysical Research Communications*, 172(3):1132-1138, 1990, published in San Deigo, CA.

Gross et al., "Cytokine-activated Endothelial Cells Express an Isotype of Nitric Oxide Synthase Which is Tetrahydrobiopterin-Dependent. Calmodulin-Independent and Inhibited by Arginine Analogs with a Rank-Order of Potency Characteristic of Activated Macrophages," *Biochemical and Biophysical Research Communications*, 178(3):823-829, 1991, published in San Diego, CA.

Schmidt et al., "Insulin Secretion from Pancreatic B Cells Caused by L-Arginine-Derived Nitrogen Oxides," *Science*, 255:721-723, 1992, published in Washington, DC.

Sakuma et al., "Identification of Arginine as a Precursor of Endothelium-Derived Relaxing Factor," *Proc. Natl. Acad. Sci. USA*, 85:8664-8667, 1988, published in U.S.A.

Stuehr & Marletta, "Induction of Nitrite/Nitrate Synthesis in Murine Macrophages by BCG Infections, Lympholines, or Interferon-$\gamma$, " *The Journal of Immunology*, 139(2):518-525, 1987, published in Baltimore, MD.

Gruetter et al., *Journal of Pharm. & Experim. Therap.*, vol. 24, No. 1 (1980) pp. 9-15.

INHIBITION OF NITRIC OXIDE-MEDIATED HYPOTENSION AND SEPTIC SHOCK WITH IRON-CONTAINING HEMOPROTEIN

FIELD OF THE INVENTION

The invention is directed to a method for the prophylaxis or treatment of an animal for systemic hypotension induced by a biological response modifier. Examples of such biological response modifiers include but are not limited to a cytokine and an endotoxin. The invention is also directed to a method for the treatment of septic shock.

BACKGROUND OF THE INVENTION

Endothelium-Derived Relaxing Factor

Endothelial cells have been shown to produce a potent vasodilator known as Endothelium-Derived Relaxing Factor (EDRF). Many naturally occurring substances which act as physiological vasodilators mediate all or part of their action by stimulating the release of EDRF. Examples of such substances include acetylcholine, histamine, bradykinin, leukotrienes, ADP, and ATP. Recent studies have identified EDRF as nitric oxide, a short lived, unstable compound (Ignarro et al., 1987, *Proc. Natl. Acad. Sci. U.S.A.* 84:9265–9269 and Palmer et al., 1987, *Nature* 327:524–526).

L-Arginine is the metabolic precursor of EDRF (Schmidt et al., 1988, *Eur. J. Pharmacol.* 154:213–216). $N^G$-methyl-L-arginine is a competitive inhibitor of the biosynthetic pathway of EDRF (Palmer et al., 1988, *Nature* 333:664–666). Administration of $N^G$-methyl-L-arginine to guinea pigs and rabbits has been shown to increase blood pressure (Aisaka et al., 1989, *Biochem. Biophys. Res. Commun.* 160:881–886). Nitric oxide (NO) appears to be synthesized from L-arginine by the enzyme, NO synthase; the coproduct is L-citrulline (Moncada et al., 1991, *J Cardiovascular Pharmacol.* 17 (Suppl. 3):S1–S9). NO is an endogenous stimulator for soluble guanylate cyclase.

Nitric oxide has been found to be produced by macrophages, endothelial cells, neutrophils, Kupffer cells and hepatocytes, murine fibroblasts stimulated with cytokines, and EMT-6 cells, a spontaneous reurine mammary adenocarcinoma cell line when treated with cytokine (reviewed in Moncada et al., 1991, *Pharmacol. Reviews* 43:109–142). Specifically, macrophage cells become activated by 12–36 hour treatments with gamma-interferon, bacterial endotoxin and various cytokines (reviewed in Collier and Vallance, 1989, *Trends in Pharmacol. Sci.* 10:427–431).

Endothelial cells in the presence of gamma-interferon, have been found to secrete large quantities of arginine-derived nitrogen oxides after activation by tumor necrosis factor (TNF) or endotoxin (Kilbourn and Belloni, 1990, *J. Natl. Cancer Inst.* 82:772–776). TNF causes marked hypotension in mammals (Tracey et al., 1986, *Gynecol. Obstet.* 164:415–422; Old, 1985, *Science* 230:630–632). Additionally, TNF is thought to mediate the vascular collapse resulting from bacterial endotoxin (Beutler et al., 1985, *Science* 229:869–871). It has recently been shown that arginine derivatives inhibit systemic hypotension associated with nitric oxide production, specifically treatment with TNF, gamma interferon, interleukin-2, and bacterial endotoxin (Kilbourn et al., U.S. Pat. No. 5,028,627, issued Jul. 2, 1991; PCT lypplication no. WO 91/04023, published Apr. 4, 1991; and Kilbourn et al., 1990, *Proc. Natl. Acad. Sci. U.S.A.* 87:3629–3632). Nitric oxide overproduction is also thought to be involved in numerous other pathogenic or potentially pathogenic syndromes. For example, some of these syndromes are thought to be associated with malaria, senescence and diabetes. The procedures of the present invention may also be used to prevent, inhibit and/or alleviate such NO-related syndromes.

Interaction of Hemoglobin with Endothelium-Derived Relaxation Factor

Nitric oxide reacts with hemoglobin to form nitrosylhemoglobin (Kosaka et al., 1989, *Free Radical Biology* 7:653–658). Nitrosylhemoglobin reacts with oxygen to yield nitrate and methemoglobin, which is rapidly reduced by methemoglobin reductase. At least part of the nitric oxide is oxidized by oxygen to $NO_2$, which is in turn converted to nitrite and nitrate.

The formation of nitrosylhemoglobin has been used to quantify nitric oxide present in mice given bacterial endotoxin, specifically by using electron paramagnetic resonance (EPR) spectroscopy to detect NO liganded to hemoglobin (Wang et al., 1991, *Life Sciences* 49:55–60). Although bacterial endotoxin induces septic shock, hypotension was not observed in the Wang et al. study. Those skilled in the art recognize that such EPR studies may be used to quantitate the binding of NO to other hemoproteins as well.

Hemoglobin has also been found to inhibit nonvascular relaxant responses to EDRF (Buga et al., 1989, *Eur. J. Pharmacol.* 161:61–72). Furthermore, hemoglobin at 1 $\mu M$ reduced and at 10 $\mu M$ abolished tie endothelium-dependent relaxation induced by acetylcholine or by A23187 in rabbit aortic rings (Martin et al., 1985, *J. Pharmacol. Exp. Ther.* 232:708–716). It was hypothesized by Martin et al. that the hemoglobin inhibits endothelium-dependent induced relaxation by binding nitric oxide.

Septic Shock

Septic shock is characterized by inadequate tissue perfusion and is usually caused by gram-negative enteric bacilli such as *Escherichia coli,* Klebsiella, Enterobacter, Pseudomanas, Serratia, and Bacteroides (see Harrison's INTERNAL MEDICINE, 10th Ed., vol.1, Petersdorf et al., eds., McGraw Hill, N.Y. 1983). Gram-negative bacilli possess endotoxin, also known as lipopolysaccharide (LPS), which is a cell-wall component that can activate leukocytes in minute amounts in the blood.

Septic shock is characterized by chills, fever, nausea, vomiting, diarrhea, and prostration. The subsequent development of septic shock is characterized by tachycardia, tachypnea, hypotension, peripheral cyanosis, mental obtundation, and oliguria. As shock progresses, oliguria persists, and heart failure, respiratory insufficiency, and coma supervene. Death usually results from pulmonary edema, generalized anoxemia secondary to respiratory insufficiency, cardiac arrhythmia, disseminated intravascular coagulation with bleeding, cerebral anoxia, or a combination of the above.

Most of the damage caused by septic shock is thought to be caused by endotoxin. It has also been hypothesized that nitric oxide plays a major role in effecting hypotension in those exposed to endotoxin (Kilbourn et al. *Biochem. and Biophys. Res. Comm.* 1991, vol. 172:1132–1138). Studies have shown that the hypotension and loss of vascular responsiveness resulting from endotoxin administration is reversed by the administration of analogues of L-arginine which inhibit nitric oxide production (Parratt and Stoclet, 1991, *Applied Cardiopulmonary Pathophysiology* 4:143-149; and Kilbourn et al., 1990, *Proc. Natl. Acad. Sci. U.S.A.* 87:3629-3632).

In certain cases, acute blood loss may cause hypotension. After initial recovery due to standard hypotension treatment, a breach of intestinal integrity may subsequently cause septic hypotension. Such a syndrome is readily treated according to the methods of the present invention.

Treatments for Septic Shock

There are currently a number of clinical procedures available for the treatment of septic shock (reviewed in Harrison's INTERNAL MEDICINE, 10th Ed., vol.1, Petersdorf et al., eds., McGraw Hill, N.Y. 1983). However each has its drawbacks. One treatment involves the replacement of blood volume with blood, plasma, or other fluids such as human serum albumin in appropriate electrolyte solutions such as dextrose saline and bicarbonate. However, large quantities of these substances are required and may amount to 8 to 12 liters in only a few hours, leading to massive shifts in fluid and electrolyte balances.

Antibiotics may also be used to treat septic shock. However, to determine the appropriate antibiotics to use, blood cultures must be taken and evaluated. Such cultures take time. Additionally, antibiotics may initially worsen shock caused by bacteria since they kill the bacteria and the dying organisms can release even more lipopolysaccharide into the body.

Vasoactive drugs such as beta-receptor stimulants (e.g. isoproterenol and dopamine) and alpha-receptor blocking agents (phenoxybenzamine and phentolamine) have also been therapeutically used since septic shock is accompanied by maximal stimulation of alpha-adrenergic receptors. However, all of these drugs may have serious side effects. In addition, studies by Stoclet et al. (*Amer. J. Physiol.* 259:H1038-1043) suggest that endotoxic shock and NO production can cause lowered sensitivity to these agents, decreasing their effectiveness. The iron hemoprotein therapy of the present invention may be used to reverse this loss of sensitivity.

Another treatment approach involves using human antiserum to *E. coli* J5, a mutant strain that produces endotoxin without the variable oligosaccharide side chains. However, since such antiserum comes from many different human donors with varying immune responses to the antigen, it cannot be rigidly standardized for effectiveness. Such antiserum may also transmit infectious agents. To circumvent these problems, monoclonal antibodies that bind to endotoxin are currently being tested in patients suffering from septic shock (reviewed in Johnston, 1991, J. NIH Res. 3:61-65). A disadvantage of this approach is that treatment of septic patients with antiendotoxin antibodies has no immediate effect on blood pressure and may not work at all if patients are not treated at an early stage.

Another approach used to treat septic shock involves administering bactericidal permeability-increasing protein (BPI), a human protein derived from neutrophil granules. This protein binds to LPS. Versions of the molecule are currently being developed (reviewed in Johnston, 1991, *J. NIH Res.* 3:61-65).

Approaches are also being developed for treating septic shock by preventing endotoxin from activating leukocytes that start the inflammatory response (reviewed in Johnston, 1991, *J. NIH Res.* 3:61-65). Examples of such approaches include administering a soluble interleukin-1 (IL-1) receptor, an IL-1 receptor antagonist, a monoclonal antibody to TNF-$\alpha$, soluble TNF receptor and a monoclonal antibody to TNF-$\alpha$ receptor. All of these approaches suffer from the fact that blockade of the cytokine receptor interaction does not have an immediate effect on nitric oxide production by NO synthase (i.e.—once induced by cytokines, NO synthase continue to produce NO even after removal of the stimulus).

The present invention involves the treatment of a nitric oxide induced malady such as hypotension by administration of an iron hemoprotein which has substantial affinity for nitric oxide and/or catalyzes nitric oxide oxidation to nitrates or nitrites. The most preferred iron hemoprotein is hemoglobin, particularly recombinant hemoglobin. Myoglobin, which also is known to bind nitric oxide may also be utilized. Additional iron hemoproteins, including certain cytochromes, e.g. are known and may be used when demonstrating the above mentioned nitric oxide-related effects. Particularly preferred hemoglobins are those which have a long circulating lifetime, e.g., those which have a poor affinity for haptoglobin. Those skilled in the art will recognize that any iron heme-containing proteins or peptides binding NO may be administered to an animal in a pharmaceutically effective amount to remove nitric oxide and prevent or treat hypotension or other NO-induced deleterious effects.

Despite previous results showing the interaction of iron hemoproteins such as hemoglobin with nitric oxide, the therapeutically effective results of the present inventive method are quite surprising and unexpected. Such a result could not have been expected in view of the fact that normal mammalian blood fluid is replete with hemoglobin contained in red blood cells which contain about 34% hemoglobin. Such cells usually constitute over 43% of the blood. Thus blood is about 15% hemoglobin. Additionally, nitric oxide is quite lipophilic and readily penetrates red blood cells. One skilled in the art would have expected that any effects of a free iron hemoprotein such as hemoglobin in the blood to remove deleterious nitric oxide would have been insignificant as compared to the effects of hemoglobin contained in red blood cells already present. The basis for the surprising and unexpectedly effective results of the present invention are incompletely understood at the present time, but, as the present invention is described, it will be clear to those of skill in the art that the free iron hemoproteins of the present invention such as hemoglobin are phenomenally effective for therapeutic purposes related to a reversal of deleterious physiological effects induced by nitric oxide in vivo.

SUMMARY OF THE INVENTION

The invention is directed to a method for the prophylaxis or treatment of an animal for systemic hypotension or other pathogenic syndromes induced by inappropriate nitric oxide production. Such hypotension may be induced by certain cytokines or a microbial toxin such as bacterial endotoxin. The method involves administering a therapeutically effective amount of an iron hemoprotein such as hemoglobin and the like. The administration is preferably intravascular, which includes intraarterial and intravenous. Other parenteral administration routes, e.g. peritoneal or intralymphatic, to name but a few, can be used for removal of undesired NO production at related sites. Enteral administration could be feasible if the hemoprotein or a derivative thereof was resistant to digestion and passed into the circulation. The animal may be, for example, a domestic mammal or a human patient. The systemic hypotension most characteristically results from abnormal production of nitric oxide induced by a cytokine or microbial toxin. A therapeutically effective amount of iron hemoprotein is an amount sufficient to bind and/or oxidize substantially all of the free nitric oxide and thus removing it from the circulation. In a preferred embodiment, the iron hemoprotein is hemoglobin or myoglobin and is administered intravascularly.

Bacterial endotoxin is a primary causative agent of septic shock. Elevated levels of nitric oxide have been found in animals in septic shock (Wang et al., 1991, *Life Sciences* 49:55-60). Therefore, the invention is also directed to a method for the treatment of septic shock in a patient comprising administering a therapeutically effective amount of an iron hemoprotein such as the preferred hemoglobin.

DETAILED DESCRIPTION OF THE INVENTION

In a major embodiment, the present invention is directed to a method for the prophylaxis or treatment of an animal for systemic hypotension induced by a biological response modifier directly or indirectly causing nitric oxide overproduction. Examples of such biological response modifiers include but are not limited to cytokines. The invention is also directed to a method for the treatment of septic shock and associated hypotension.

Preparation of Hemoglobin

The starting material, unmodified hemoglobin, may be obtained using procedures known in the art (see for example, PCT Application Publication No. WO 88/03408, published May 19, 1988; U.S. Pat. No. 4,001,401; Feola et al., 1983, *Surgery Gynecology and Obstetrics* 157:399-408; De Venuto et al., 1979, *Surgery Gynecology and Obstetrics* 149:417-436). For example, unmodified stroma-free hemoglobin may be obtained as follows: (a) obtaining whole blood; (b) separating red blood cells from other components of whole blood; (c) isolating the hemoglobin from the erythrocytes; and (d) separating the hemoglobin from stroma and other impurities.

Stroma-free hemoglobin can be prepared by starting with erythrocytes in freshly drawn, outdated, or frozen packed cells or whole blood. The blood should be drawn in a sterile fashion into containers with sufficient anticoagulant activity to prevent clot formation.

In one embodiment, blood cells are washed in a saline solution and centrifuged to separate red blood cells from white blood cells as well as to additionally remove free proteins (Feola et al., 1983, *Surgery Gynecology and Obstetrics* 157:399-408). In another embodiment, the red cells may be separated from other blood cells by passing through a semi-continuous type centrifuge as described in PCT Application Publication No. WO 88/03408, published May 19, 1988.

Hemoglobin may be isolated in one embodiment by diluting the red blood cell solution in water or an organic solvent at 2°-100° C. to separate the hemoglobin in red blood cells from all cell debris (PCT Application Publication No. WO 88/03408, published May 19, 1988; U.S. Pat. No. 4,001,401; Feola et al., 1983, *Surgery Gynecology and Obstetrics* 157:399-408). In another embodiment, the hemoglobin is precipitated as a zinc complex by the addition of a zinc salt to a hemoglobin solution (De Venuto et al., 1979, *Surgery Gynecology and Obstetrics* 149:417-436).

The isolated hemoglobin, in another embodiment, may be purified by ultrafiltration through for example a 0.5 micron filter which retains the cellular components and passes the hemoglobin.

Hemoglobin may also be obtained through other procedures known in the art. For example, bacterial strains (see for example Nagai and Hoffman, U.S. Pat. No. 5,028,588, issued Jul. 2, 1991) or yeast (see for example PCT Application Publication No. WO90/13645, published Nov. 15, 1990), or other eukaryotic organisms may be engineered to produce hemoglobin by recombinant DNA techniques. Recombinant hemoglobin is thought to be particularly advantageous because it can be readily produced in large quantities and because utilization of such recombinant hemoglobin obviates the possibility of blood-borne infection such as that by various viruses or retroviruses.

The hemoglobin may be for example, any human hemoglobin, including but not limited to HbA (alpha$_2$beta$_2$), HbA2 (alpha$_2$delta$_2$), HbF (alpha$_2$gamma$_2$), Hb Barts (gamma$_4$), HbH (beta$_4$), and Hb Portland I (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$); as well as any other animal hemoglobin, e.g. bovine or porcine hemoglobin.

The hemoglobin used in the method of the present invention may be chemically modified using procedures known in the art to increase tetramer stability and/or lower oxygen affinity. Examples of chemical modifications to increase the tetramer stability include but are not limited to crosslinking with polyalkylene glycol (Iwashita, U.S. Pat. Nos. 4,412,989 and 4,301,144), with polyalkylene oxide (Iwasake, U.S. Pat. No. 4,670,417); with a polysaccharide (Nicolau, U.S. Pat. Nos. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061,736); with insulin (Ajisaka, U.S. Pat. No. 4,377,512); and with a crosslinking agent so that the hemoglobin composition is intramolecularly crosslinked between lys 99 alpha$_1$ and lys 99 alpha$_2$ (Walder, U.S. Pat. No. 4,598,064). Examples of chemical modifications to decrease the oxygen affinity of isolated hemoglobin include but are not limited to polymerization with pyridoxal phosphate (Sehgal et al., 1984, *Surgery,* 95:433-438) and using reagents that mimic 2,3-DPG (Bucci et al., U.S. Pat. No. 4,584,130).

In a further embodiment, the hemoglobin used in the method of the present invention may be a hemoglobin variant, a hemoglobin comprising a globin chain from a nucleotide sequence which has been altered in such a fashion so as to result in the alteration of the structure or function of the hemoglobin, but so that the hemoglobin still remains functionally active as defined by the ability to reversibly bind to oxygen (or nitric oxide, of course). Categories of hemoglobin variants include but are not limited to variants which autopolymerize; variants in which the tetramer does not dissociate under physiological conditions i-n vivo (e.g. Hb Rainier, beta-145 tyrosine is replaced by cysteine); variants with lowered intrinsic oxygen affinity, i.e. a hemoglobin having a P50 of at least about 10 Mm Hg under physiological conditions (e.g. Hb Chico, beta-66 lysine is replaced by threonine; Hb Raleigh, beta-1 valine is replaced by alanine; Hb Titusville, alpha-94 aspartate to asparagine; Hb Beth Israel (beta-102 asparagine is replaced with serine; and Hb Kansas, beta-102 asparagine to threonine; variants that are stable in alkali (e.g. Motown/Hacettepe, beta-127 or glutamine is replaced with glutamic acid); variants that are stable in acid; variants which have a lowered binding affinity to haptoglobin; variants with an increase intrinsic oxygen affinity, i.e. a hemoglobin having a $P_{50}$ of at most about 1 mm Hg under physiological conditions (e.g. HbA Deer Lodge, beta-2 histidine is replaced with arginine, Labossiere et al., 1972, Clin. Biochem. 5:46–50; HbA Abruzzo, beta-143 histidine is replaced with arginine, Tentori et al., 1972, Clin. Chim. Acta 38:258–262; and HbA McKees Rocks, beta-145 tyrosine is replaced with a termination sequence, Winslow et al., 1976, J. Clin. Invest. 57:772–781).

Acid stable hemoglobin variants may include those that replace the histidine at the alpha-103 position with an amino acid is not ionized in acid (Perutz, 1974, Nature 247:341). Examples of such amino acids include serine, threonine, leucine, and alanine.

Haptoglobin nonbinding hemoglobin variants are those with variation in the alpha-121-127 sequence. This sequence has been shown to be involved in the binding of haptoglobin which is believed incident to increased circulatory clearance (McCormick and Atorssi, 1990, J. Prot. Chem. 9:735).

The globin variants may be produced by various methods known in the art. The manipulations which result in their production can occur at the gene or protein level. The globin may be altered at the gene level by site-specific mutagenesis using well-known procedures. One approach which may be taken involves the use of synthetic oligonucleotides to construct variant globins with base substitutions. In one embodiment, a short oligonucleotide containing the mutation is synthesized and annealed to the single-stranded form of the wild-type globin gene (Zoller and Smith, 1984, DNA 3:479–488). The resulting short heteroduplex can serve as primer for second strand synthesis by DNA polymerase. At the 5' end, a single stranded nick is formed which is closed by DNA ligase. In another embodiment, two complementary oligonucleotides are synthesized, each containing the mutant sequence. The duplex that forms after annealing these complementary oligonucleotides, can be joined to a larger DNA molecule by DNA ligase provided that the ends of both molecules have complementary single-stranded "sticky" ends. Another approach which may be taken involves introducing a small single-stranded gap in the DNA molecule followed by mis-repair DNA synthesis i.e., the misincorporation of a non-complementary nucleotide in the gap (Botstein and Shortle, 1985, Science 229:1193). The incorporation of a thiol nucleotide into the gap may minimize the excision of the non-complementary nucleotide. Alternatively, a globin variant may be prepared by chemically synthesizing the DNA encoding the globin variant using procedures known in the art (see for example Froehler, 1986, Nucl. Acids Res. 14:5399–5407 and Caruthers et al., 1982, GENETIC ENGINEERING, J. K. Setlow and A. Hollaender eds., Plenum Press, New York, vol. 4, pp. 1–17). In a preferred embodiment, fragments of the variant globin-coding nucleic acid sequence are chemically synthesized and these fragments are subsequently ligated together. The resulting variant globin-coding strands may be amplified using procedures known in the art, e.g. PCR technology, and subsequently inserted into a cloning vector as described in, e.g., PCT Application Publication No. WO90/13645, published Nov. 15, 1990). In specific embodiments, site-specific mutants may be created by introducing mismatches into the oligonucleotides used to prime the PCR amplification (Jones and Howard, 1990, Biotechniques 8:178–180).

Manipulations of the globin sequence may be carried out at the protein level. Any of numerous chemical modifications may be carried out by known techniques including but not limited to specific chemical cleavage by cyanogen bromide, trypsin, chymotrypsin, papain, or V8 protease, $NaBH_4$ acetylation, formulation, oxidation, reduction; etc. Alternatively, the variant globin protein may be chemically synthesized using procedures known in the art, such as commercially available peptide synthesizers and the like. Such standard techniques of polypeptide synthesis can be found described in such publications as Merrifield, 1963, J. Chem. Soc. 85:2149–2154 and Hunkapillar et al., 1984, Nature (London) 310:105–111).

Treatment of Hypotension and Septic Shock with Hemoglobin

The hemoglobin prepared according to the procedures described above may be used for the prophylaxis or treatment of systemic hypotension or septic shock induced by internal nitric oxide production. Such internal nitric oxide production may result from the treatment of an animal with a cytokine which includes but is not limited to tumor necrosis factor, interleukin-1, and interleukin-2, in the case of systemic hypotension. In a specific embodiment, hemoglobin may be used for prophylaxis or treatment of systemic hypotension in a patient induced by chemotherapeutic treatment with such cytokines. In septic shock, the production of nitric oxide results from the exposure of an animal to a bacterial endotoxin. Viral, fungal or enterotoxin-producing bacteria may also be found to directly or indirectly induce NO overproduction alleviatable by administration of the hemoproteins of the present invention.

The preferred iron hemoprotein, hemoglobin, used in the present invention is mixed with a pharmaceutically acceptable carrier. The pharmaceutical carriers are physiologically compatible buffers as Hank's or Ringer's solution, physiological saline, a mixture consisting of saline and glucose, heparinized sodium-citrate-citric acid-dextrose solution, and the like. The hemoglobin for use in the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the hemoglobin may be mixed with water soluble and physiologically acceptable polymeric plasma substitutes, examples of which include polyvinyl alcohol, poly(ethylene oxide), polyvinylpyrrolidone, and ethylene oxide-polypropylene glycol condensates and the like.

Techniques and formulations for administering the compositions comprising iron hemoprotein generally may be found in *Remington's Pharmaceutical Sciences*, Meade Publishing Col., Easton, Pa., latest edition. In a preferred embodiment, the hemoglobin is administered intravascularly. The amount of iron hemoprotein administered, the effective amount, is an amount sufficient to bind to substantially all of the nitric oxide present, thus removing free nitric oxide from circulation. Such an effective amount is generally in a range of from about 0.1 g/kg body weight to about 10 g/kg body weight.

The following examples are presented to illustrate a best mode and preferred embodiments of the present invention and are not meant to limit the claimed invention unless otherwise specified.

EXAMPLE I

Abrogation of Blood Pressure Decline

Experiments were carried out on conditioned mongrel dogs weighing 23-28 kg. Animal care was in accordance with the recommendations of the American Association for Accreditation of Laboratory Animal Care and met all standards prescribed by the *Guide for the Care and Use of Laboratory Animals* (Committee on Care and Use of Laboratory Animals (1978) *Guide for the Care and Use of Laboratory Animals* (Natl. Inst. Health, Bethesda, Md.) DHEW Publ. No. (NIH) 78-83.

The dog was fasted overnight before the day of the experiment and was anesthetized with pentobarbital (25 mg/kg, i.v.), orotracheally intubated and ventilated with a Harvard pump at a nominal rate of 12 breaths per minute and a tidal volume of 15 ml/kg. The dog was instrumented with a cordis for the introduction of a Swan-ganz catheter for measurement of central venous and pulmonary arterial pressures as well as an arterial line for continuous blood pressure monitoring via a computer driven analog to digital processor.

After the blood pressure and heart rate was stabilized, endotoxin was administered to the dog as a bolus injection (50 μg/kg, i.v. in 10 ml DPBS. After the onset of hypotension, a rapid infusion of 50 ml hemoglobin (5.0 g commercially available bovine hemoglobin/100 ml) over 20 seconds was administered by a central venous catheter. Cardiovascular changes were monitored for an additional 12 hrs. after hemoglobin administration.

Figure 1:
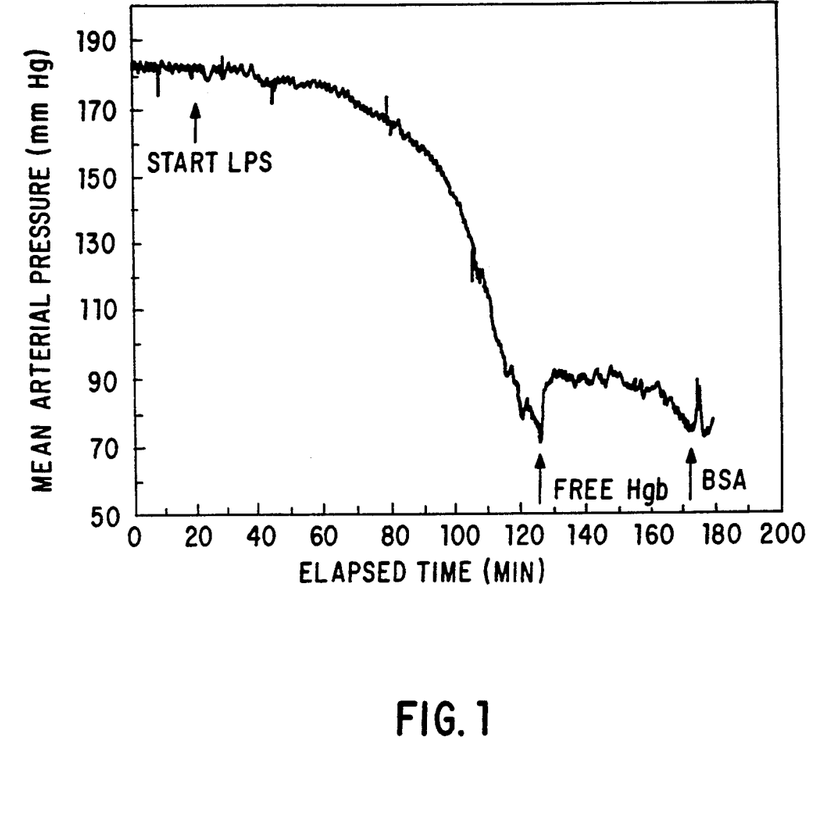
FIG. 1 shows the effect of hemoglobin on endotoxin-induced hypotension in a dog. The endotoxin-induced mean arterial decline is interrupted by administration of hemoglobin.

A tracing depicting endotoxin-induced hypotension, its inhibition by hemoglobin, and subsequent administration of bovine serum albumin (5 grams) is shown in FIG. 1. Mean arterial blood pressure declined from 160 mm Hg to 70 mm Hg two hours after endotoxin administration. The hemoglobin (HgB) was subsequently administered as an intravenous bolus. The blood pressure drop was abrogated by this administration and the hypotension was partially reversed. This effect lasted approximately 45 minutes before the blood pressure decline resumed. The subsequent decline was only slightly influenced by the administration of 5 grams of bovine serum albumin (BSA). On repetition of this experiment, substantially the same results were obtained.

EXAMPLE 2

Binding of NO by Myoglobin

Nitric oxide formation by endothelial cell cytosol was measured by a novel kinetic 96-well microplate assay. The assay is based on the capture of NO by $Fe^{2+}$-myoglobin (Mb) which is subsequently oxidized to $Fe^{3+}$-myoglobin. The process of heme oxidation was continuously measured in a kinetic microplate reader (Molecular Devices, Menlo Park Calif.) as the rate of change in $OD_{405}$-$OD_{650}$. Data points were collected from all 96 wells every 16 sec. for 30 minutes at 250° C. with shaking prior to each OD measurement. The slope of the best fit regression line (OD/min) was used to calculate the rate of NO-synthesis. OD/min measurements were converted to pmoles NO/min by dividing by the increase in $OD_{405}$-$OD_{650}$ measured upon complete oxidation of 1 pmole of reduced Mb with a 10-fold molar excess of potassium ferricyanide. Under the conditions employed, the efficiency of NO capture by Mb approached 100%; neither doubling nor halving the concentration of Mb influenced the Mb oxidation rate. All samples contained 5-30 μl of endothelial cell cytosol (1-6 mg protein/ml) and final concentrations of 5 μM Mb, 500 μM L-arginine, 500 μM NADPH and 80 Mm TRIS, pH 7.6.

$Fe^{2+}$-Myoglobin Preparation: 2 Mm myoglobin (from horse skeletal muscle, sigma) was reduced with a sodium dithionite and immediately applied to a Sephadex G-25 column, followed by elution with 50 Mm TRIS buffer, Ph 7.6. Mb was aliquoted and stored at −700° C. for up to 2 months prior to use. The usefulness of this iron hemoprotein for nitric acid removal is thus clearly shown.

Various references are cited above, the disclosures of which are incorporated in pertinent part by reference herein for the reasons cited.

The invention described and claimed herein is not to be limited in scope by the specific embodiments disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

What is claimed is:

1. A method for alleviating deleterious nitric-oxide induced effects in an animal, the method comprising administering a therapeutically effective amount of an iron hemoprotein to said animal.

2. A method of reducing nitric oxide levels induced in an animal by a cytokine or by endotoxin, the method comprising administering to said animal an iron hemoprotein in an amount effective to bind or oxidize nitric oxide.

3. A method for treatment of systemic hypotension in a patient induced by chemotherapeutic treatment with a cytokine, the method comprising administering a therapeutically effective amount of an iron hemoprotein to said patient.

4. A method for treatment of systemic hypotension in a septic patient caused by endotoxin-induced nitric oxide production comprising intravascularly administering an amount of an iron hemoprotein sufficient to bind or oxidize substantially all of the nitric oxide produced.

5. The method of claim 1, 2, 3 or 4 where the iron hemoprotein is hemoglobin or myoglobin.

6. The method of claim 1, 2, 3 or 4 where the amount is from 0.1 to 10 g/kg body weight.

7. The method of claim 1, 2, or 3 wherein the administering is intravascular.

8. The method of claim 1 where the deleterious nitric oxide-induced effect is systemic hypotension.

9. A method for treatment of an animal for systemic hypotension caused by nitric oxide comprising administering a therapeutically effective amount of hemoglobin.

10. The method of claim 9 where the nitric oxide is induced by a cytokine.

11. The method according to claim 10 where the cytokine is tumor necrosis factor, interleukin-1, or interleukin-2.

12. A method for thee treatment of an animal for systemic hypotension caused by endotoxin-induced nitric oxide production comprising administering a therapeutically effective amount of hemoglobin.

13. A method for treatment of systemic hypotension in a patient caused by nitric oxide production induced by a cytokine selected from the group consisting of tumor necrosis factor, interleukin-1, and interleukin-2 comprising administering an amount of hemoglobin sufficient to bind or oxidize substantially all of the nitric oxide produced.

14. The method of claim 9, 12 or 13 where the amount is from 0.1 to 10 g/kg body weight.

15. The method of claim 9, 12 or 13 where the administering is intravascular.

* * * * *

UNITED STATES PATENT AND TRADEMARK OFFICE
CERTIFICATE OF CORRECTION

PATENT NO. : 5,296,466
DATED : March 22, 1994
INVENTOR(S) : Robert G. Kilbourn et al.

It is certified that error appears in the above-indentified patent and that said Letters Patent is hereby corrected as shown below:

```
In claim 12, column 11, line 13 delete "thee" and insert
--the--.
```

Signed and Sealed this

Twenty-third Day of August, 1994

Attest:

BRUCE LEHMAN

*Attesting Officer*   *Commissioner of Patents and Trademarks*